US008536226B2

(12) United States Patent
Eisinger et al.

(10) Patent No.: US 8,536,226 B2
(45) Date of Patent: Sep. 17, 2013

(54) METHODS FOR THE TREATMENT OF DERMATOLOGICAL DISORDERS

(75) Inventors: Magdalena Eisinger, Demarest, NJ (US); Fa Zhang, Belle Mead, NJ (US)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

(21) Appl. No.: 13/546,646

(22) Filed: Jul. 11, 2012

(65) Prior Publication Data
US 2012/0283330 A1 Nov. 8, 2012

Related U.S. Application Data

(62) Division of application No. 12/389,687, filed on Feb. 20, 2009, now Pat. No. 8,247,453.

(60) Provisional application No. 61/030,253, filed on Feb. 21, 2008.

(51) Int. Cl.
*A61K 31/17* (2006.01)
(52) U.S. Cl.
USPC ........... 514/587; 514/342; 514/363; 514/361; 514/370; 548/125; 548/128; 564/17
(58) Field of Classification Search
USPC ......... 514/587, 342, 363, 361, 370; 548/125; 548/128; 564/17
See application file for complete search history.

(56) References Cited

U.S. PATENT DOCUMENTS

| 6,093,733 | A | 7/2000 | Villalobos et al. |
| 6,294,534 | B1 | 9/2001 | Nargund et al. |
| 6,410,548 | B2 | 6/2002 | Nargund et al. |
| 6,500,956 | B1 | 12/2002 | Geissler et al. |
| 6,911,477 | B2 | 6/2005 | Villalobos et al. |
| 7,049,331 | B2 | 5/2006 | Eisinger et al. |
| 7,319,107 | B2 | 1/2008 | Eisinger et al. |

(Continued)

FOREIGN PATENT DOCUMENTS

| DE | 131373 | 6/1978 |
| EP | 1444215 B1 | 8/2004 |

(Continued)

OTHER PUBLICATIONS

Abraham, W., et al. "Formamidinyl lsothiocyantes-III1. Addition of Necleophilic Partners to Formamidinoyl Isothiocyanates", Tetrahedron, vol. 29, No. 5 pp. 699-705 (1973).
Adan, R., et al. "Differential Effects of Melanocortin Peptides on Neural Melanocortin Receptors", Molecular Pharmacology (1994) pp. 1182-1190, vol. 46.
Adan, R., et al. "Melanocotin Receptors Mediate α-MSH Stimulation of Neurite Outgrowth in Neuro 2A Cells", Molecular Brain Research (1996) pp. 37-44, vol. 36.
Barbier, B., et al. "Crystal Structure of 2-benzyl-3-phenyl-5-phenlimino-delta3-1,2,4-this-diazoline, C21H17N3S" (1998), pp. 741-742, vol. 213.
Barnikow, G., et al. "Regarding the Oxidative Cyclization of Imidoyl-Thioureas1", Z. Chem, (1972), pp. 130, vol. 12, No. 4.
Bijlsma, W., et al. "The Enhanced Recovery of Sensorimotor Function in Rats is Related to the Melantropic Moiety of ACTH/MSH Neuropepties", European Journal of Pharmacology (1983) pp. 231-236, vol. 92.
Bligh, E., et al. "A Rapid Method of Total Lipid Extraction and Purification", Canadian Journal of Biochemistry and Physiology, vol. 37, No. 6, Aug. 1959, pp. 911-917.
Chen, W., "Exocrine Gland Dysfunction in MC5-R-Deficient Mice: Evidence for Coordinated Regulation of Exocrine Gland Function by Melanocortin Peptides", Cell (1997), pp. 788-798 vol. 91.
Chetia, et al., (1985): STN International CAPLUS database (Columbus, Ohio), Accession No. 1985:471257.
Chetia, J., et al. "One-Pot Synthesis of 2-Aryl-3-Phenyl (benzyl)-5-Phenylimino-delta4-1,2,4-Thiadiazolines Using N-Chlorosuccinimide", Synthesis Communications, Jan. 1985. pp. 83-84.
Cheng, et al., "Relationship Between . . . " Biochem.Pharmacol., 22:3099, 1973.
Chhajlani, V., et al. "Molecular Cloning of a Novel Human Melanocortin Receptor" Biochemical and Biophysical Research Communications (1993) pp. 866-873, vol. 1.
Cone, R., et al. "The Melanocortin Receptors" (2000) pp. 339-472, Human Press, Inc. Totowa, NJ.
Ebling, F., et. al. "The Synergistic Action of α-Melanocyte-Stimulation Hormoneand Testosterone on the Sebaceous, Prostate, Preputial, Harderian and Lachrymal Glands, Seminal Vesicles and Brown Adipose Tissue in the Hyophysectomized-Castrated Rat", J. Endocr. (1975) pp. 407-412, vol. 66.
Fan, W., et al. "Role of Melanocortingenic Neurons in Feeding and the Agouti Obesity Syndrome" Nature (1997) pp. 165-168, vol. 385.
Fawzi, A., et al. "SCH-202676: An Allosteric Modular of Both Agonist and Antagonist Binding to G. Protein-Coupled Receptors", Molecular Pharmacology (2001) pp. 30-33, vol. 59, No. 1.

(Continued)

Primary Examiner — Savitha Rao

(57) ABSTRACT

The present invention is directed to the use of a compound of formula (I)

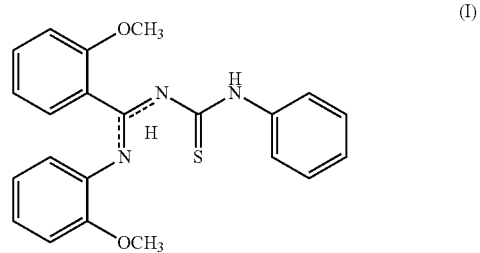

or pharmaceutically acceptable salt thereof, for the treatment of disorders mediated by the melanocortin-5 receptor, particularly dermatological disorders; and further directed to pharmaceutical compositions containing the compound of formula (I) or a pharmaceutically acceptable salt thereof.

7 Claims, No Drawings

(56) References Cited

U.S. PATENT DOCUMENTS

| | | | |
|---|---|---|---|
| 7,375,123 | B2 | 5/2008 | Eisinger et al. |
| 7,435,429 | B2 | 10/2008 | Modak et al. |
| 7,786,311 | B2 | 8/2010 | Eisinger et al. |
| 2010/0273838 | A1 | 10/2010 | Cui et al. |
| 2010/0280079 | A1 | 11/2010 | Eisinger et al. |

FOREIGN PATENT DOCUMENTS

| | | |
|---|---|---|
| EP | 1446394 B1 | 8/2004 |
| JP | 60-11481 | 1/1984 |
| JP | 2-173165 | 7/1990 |
| WO | 99/55675 A1 | 11/1999 |
| WO | 99-55679 A1 | 11/1999 |
| WO | 99/64002 A1 | 12/1999 |
| WO | 00/24725 A1 | 5/2000 |
| WO | 01/55107 A2 | 8/2001 |
| WO | 02/35340 A1 | 5/2002 |
| WO | 03/040117 A | 5/2003 |
| WO | 03/040118 A1 | 5/2003 |
| WO | 2009/105647 | 8/2009 |

OTHER PUBLICATIONS

Gantz, I., et al. "Molecular Cloning, Expression and Gene Localization of a Fourth Melanocortin Receptor" J. Biol. Chem (1993), pp. 15174-15179, vol. 268.
Goerdeler, J., et al. "Über die Zerfallsprodukte con Imno-delta3-1,2,4-thiadiazolinen" .Chem. Ber.112, pp. 1288-1296 (1979) (With English Translation).
Goerdeler, J., et al. "Herstellung von Acylheterocumulenen aus Funfglidrigen Ringen mit Hilfe von Phosphinen", Chem. Ber. (1974) pp. 502-507 vol. 107 (With English Abstract).
Goerdeler, J., et al. "Uber Imidoyl-Isothiocyanate, II2)" Chem. Ber. 101, pp. 3475-3490 (1968) (With English Translation).
Goerdeler, J., et al. "Reaktionene von 5-limino-1,2,4-thiadiazolinen mit Heterocummulenen (Praparative Gesichtspunkte)", Chem Ber. (1979) pp. 517-531, vol. 112 (English Abstract on First Page).
Goerdelerr, J., et al. "Reaktion von Heterocumulenen mit 5-Ahoxy-3-Phenylimino-3H-1,2,4-Dithiazol",. Chem. Ber. (1976) pp. 848-854, vol. 109 (With English Abstract).
Goerdeler, J., et al. "Herstellung von (N-Alkylbenzimoidoyl)-und (N-Arylbenzimidoyl) carbodiimiden:ihre Umlagerung zu Aminochinazolinen und Dihydro-1, 3, 5-Triazinen", Chem. Ber. (1986) pp. 3737-3748, vol. 11 (With English Abstract).
Greene, R., et al. "Anatomical Variation in the Amount and Composition of Human Skin Surface Lipid*", Journal of Investigative Dermatology (1970) pp. 240-247, Vo. 54.
Hagiwara, K., et al. "Synthesis and Fungicidal Activity of A3-1, 2-4-Thiadizolines" Journal of Pesticide Science (1992) pp. 251-259, vol. 17.
Huszar, D., et al. "Targeted Disruption of the Melanocortin-4-Receptor Results in Obesity in Mice", Cell, vol. 88, pp. 131-141 (1997) vol. 88.
L'Abbe, G. et al. "5-Imino-Delta3-1,2,4-Thiadiazoline Derivatives With a Linear N-S . . . O Grouping, Synthesis and Crystal Structure", J. Heterocyclic Chem. Nov. 1981 pp. 1309-1317, vol. 18.
Liebscher, J. et al. "Oxidation-Assisted Synthesis of N-Imidoyl-Guanidines from N-Imidoyl-Thioureas", Z. Chem. (1985) pp. 362-363, vol. 25, No. 10.
Mountjoy, K., et al. "Localization of the Melanocortin-4 Receptor (MCR4-R) in Neuroendocrine and Autonomic Control Circuits in the Brain", Molecular Endocrinology. (1994) pp. 1298-1308.
Nair, M., et al. "Oxidation of N-Phenyl-N-Phenylthiocarbamoylbenzamidines With Sulphuryl Chloride & Bromine", Indian Journal of Chemistry, May 1980, pp. 335-337, vol. 19B.
Nair, M. et al. (1980) STN International CAPLUS database Accession No. 1981:15644.
Neidlein, R., et al. "Zum Reaktionsverhalten Von N-Acyl-S-Chlorisothiocarbamoylchloriden" Tetrahedrom (1971), pp. 4117-4124, vol. 27 (English Abstract on First Page).
Ng, T., "Studies on Hormonal Regulation of Lipolysis and Lipogenesis in Fat Cells of Various Mammalian Species", Comparative Biochemistry, (1990), pp. 441-443 vol. 97.
Rajappa, S., et al. "A General Synthesis of Thiazoles, Part 3. Comparative Evolution of Different Functionalised Tioureas As Precursors", J.C.S. Perkin I, May 1978, pp. 1762-1764.
Ramachandran, J., et al. "Divergent Effects of Adrenocorticotropin and Melanotropin on Isolated Rat and Rabbit Adipocytes", (1987), pp. 339-346, vol. 428.
Richter, W., et al. "Lipolytic Potency of Proopiomelaocorticotroin Peptides In Vitro", Neuropeptides (1987) pp. 59-71, vol. 9.
Strand, F., et al. "Melanocortins As Factors in Somatic Neuromusclar Growth and Regrowth", Pharmac. Therapeutics (1994) pp. 1-27, vol. 62.
Thiboutot, D., et al. "The Melanocortin 5 Receptor is Expressed in Human Sebaceious Glands and Rat Preputial Cells", J. Invest. Dermatology (2000) pp. 614-619 vol. 115(4).
Thody, A., et al. "Control and Function of Sebaceous Glands", Physiological Reviews (1989) pp. 383-415, vol. 69.
Thody, A., et al. "Control of Sebum Secretion by the Posterior Pituitary", Nature, (1972), pp. 346-347 vol. 237.
Thody, A., et al. "Control of Sebaceous Gland Function in the Rat by α-Melanocyte-Stimulating Hormone", J. Endocr. 64 (1975), pp. 503-510 vol. 64.
Van Der Neut, R., et al. "Stimulation by Melanocortins of Neurite Outgrowth From Spinal and Sensory Neurons in Vitro", Peptides (1992) pp. 1109-1115, vol. 13.
Van Der Zee, C., et al. "α-MSH and ORG.2766 in Peripheral Nerve Regeneration: Different Route of Delivery", European Journal of Pharmacology (1988) pp. 351-357, vol. 147.
Wikberg, J. "Melanocortin Receptors: New Opportunities in Drug Recovery", Exp. Opinion, Therapeutics Patents (2001), pp. 61-76, vol. 11, No. 1.
Zhang, L., et al. "Melanocortin-5-Receptor: A Marker of HumanSebocyte Differentiation", Peptides (2006) vol. 27, No. 2, pp. 413-420.
Zhang, F., et al. "Non-Enzymatic Reduction of a 1,2,4-Thiadiazolium Derivative", Bioorganic & Medicinal Chemistry Letters (2008) vol. 18, No. 6, pp. 2172-2178.
Zyabrev, V.S., et al. "Chlorination of Imidoyl Isothiocyanates", Ukrainskii Kmicheskii Zhurnal; (1995) pp. 55-61, vol. 61, No. 5.
U.S. Office Action issued in U.S. Appl. No. 12/765,981 dated Dec. 28, 2012.
Z. Chem, vol. 25 (1985) No. 10, pp. 362-363 with English language translation.
PCT International Search Report dated Jan. 31, 2003, for PCT Appln. No. PCT/US02/35340.
International Search Report dated Jan. 31, 2003 for Application No. PCT/US/02135365.
International Search Report dated May 6, 2009 for Application No. PCT/US2009/034684.
International Search Report dated Jun. 24, 2010 for Application No. PCT/US2010/032186.
Pan, et al. (2003) "The Synthesis of Aminobenzothiazoles from 2,3-Biaryl-5-anilino Δ 3-1,2,4-thiadiazolines", Sunthetic Communications, vol. 33, No. 12 pp. 2053-2060.
U.S. Appl. No. 13/835,418, filed Mar. 15, 2013.
U.S. Appl. No. 13/836,370, filed Mar. 15, 2013.

METHODS FOR THE TREATMENT OF DERMATOLOGICAL DISORDERS

RELATED APPLICATIONS

The present application is a divisional application of copending U.S. patent application having Ser. No. 12/389,687 filed on Feb. 20, 2009, which is claiming priority of provisional application having Ser. No. 61/030,253, filed on Feb. 21, 2008.

FIELD OF THE INVENTION

The present invention is directed to the use of a compound of formula (I)

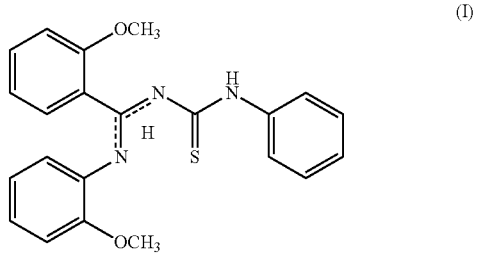

or pharmaceutically acceptable salt thereof, for the treatment of disorders mediated by the melanocortin-5 (MC5) receptor, particularly dermatological disorders; and further directed to pharmaceutical compositions containing the compound of formula (I) or a pharmaceutically acceptable salt thereof.

BACKGROUND OF THE INVENTION

Melanocortins are neuropeptides that arise from pro-opiomelanocortin (POMC), which is most prevalently expressed in the arcuate nucleus of the hypothalamus, pituitary lobes, and the nucleus tractus solarius of the brainstem. [Gantz, I., et al., *Molecular Cloning, Expression, and Gene Localization of a Fourth Melanocortin Receptor*, J. Biolog. Chem., 1993, 268, 15174-15179.] These peptides include ACTH, α-MSH, β-MSH, $\gamma_{1-3}$-MSH, and synthetic analogue NDP-αMSH (Wikberg, J E S, *Melanocortin receptors: new opportunities in drug discovery*, Exp. Opin. Ther. Patents, 2000, 11(1), 61-76).

These peptides bind to five types of melanocortin receptors (MC1-MC5), which are G-protein coupled receptors that all positively modulate adenylate cyclase. The MC4 and MC5 receptors are widely distributed in the brain and spinal cord, whereas the MC3 receptor is located mainly in the hypothalamus. [Gantz, I., et al., supra.] The MC4 receptor is selectively activated by αMSH and can induce neurite outgrowth in Neuro 2A cells. (Adan R. A. H, et al., Molecular Brian Research, 1996, 36, pp 37-44; Mountjoy, K. G., Mortud, M. T., Low, M. J., Simerly, R. B. and Cone, R. D., Mol. Endocrinol., 1994, 8, pp 1298-1308). ACTH is a less potent activator of the MC4 receptor than α-MSH. (Adan, R. A. H., Cone, R. D., Burbach, J. P. H. and Gispen, W. H., mol. pharmacol., 1994, 46, pp 1182-1190). The MC5 receptor is activated, in order of degree, by NDP-α-MSH>ACTH (1-24) ≧α MSH ACHT (1-39)=β MSH>>γMSH (*The Melanocortin Receptors*, Cone, R. D., Editor, Human Press Inc., Totowa, N.J., 2000, Chen, W., pp 449-472)

The melanocortins αMSH and ACTH are also known for their ability to stimulate pigmentation and adrenal glucocorticoid secretion, respectively. The role of melanocortins, particularly αMSH, in the regulation of sebaceous gland activity (an exocrine gland with holocrine type of secretion) was shown originally in rats. More particularly, the studies showed that removal of the intermediate lobe of the pituitary (which produces the POMC peptides) resulted in decreased sebaceous lipid production, with complete restoration to normal levels after replacement therapy with αMSH (Thody, A. J. and Shuster, *Nature,* 237, 346-347, 1972). In a study of rats following total hypophysectomy, treatment with αMSH resulted in an increase of sebum production, although full restoration of sebum production was achieved only after treatment with a combination of GASH and testosterone (Thody, A. J., Shuster, S., J. *Endocr.* 64, 503-510, 1975; Ebling, F. J., Ebling, E., Randall, V. and Skinner, J., *J. Endocr.* 66, 407-412, 1975). Knock-out mice where the MC5 receptor was deleted were observed to display a severe defect in water repulsion and thermo-regulation, due to decreased production of sebaceous lipids (Chen, W. Kelly, M. A., Opitz-Araya, X., Thomas, R. E., Low, M. J., and Cone, R., *Cell,* 91, 788-798, 1997).

The MC5 receptor is known to be expressed in human sebaceous glands, and may be involved in the regulation of human sebaceous lipid synthesis. The human MC5 receptor has been cloned and characterized (Chhajlani, V., Muceniece, R., Wikberg, JES., *Biochem. Biophys. Res. Commun.* 195, 866-873, 1993). Moreover, presence of MC5 receptor m RNA in human sebaceous glands has been shown by RT-PCR and the protein was detected by immunohistochemistry and Western blot analysis (Thiboutot, D., Sivarajah, Gililand, K., Cong, Z. and Clawson, G., *J. Invest. Dermatol.* 115(4), 614-619, 2000).

Human sebum differs in its composition from other mammals. The main lipids in human sebum are triglycerides, wax esters and squalene (Greene, R. S., Downing, D. T., Poci, P. E., Strauss, J. S., *JID* 54, 240-247, 1970).

Squalene, for instance, is not found in many mammals with the exception of otter and beaver. Triglycerides, which are a major component of human sebum, are poorly represented in other species and in many (e.g. chimpanzee) appear to be totally absent (Thody, A. J., Shuster, S., *Physiolog. Rev.* 69, 383-415, 1989). Moreover, melanocortins can have different effects on cells from different species. For example both αMSH ($EC_{50}$=3.7 nM) and ACTH ($EC_{50}$=16.4 nM) are potent lipolytic agents for rabbit adipocytes, whereas in the rat only ACTH ($EC_{50}$=1.34 nM) has potent lipolytic activity (Ramachadran, J., Lee, V., 428, 339-346, 1987; Richter, W. O., Schwandt, P., *Neuropeptides* 9, 59-74, 1987). Despite lipolytic activity in rodents and rabbits, ACTH has very little effect on lipolysis in isolated human and non-human primate adipocytes, even at concentrations as high as 1 μM (Ng, T. B. *Comparative Biochem.* 97, 441-446, 1990). Thus defining the role of melanocortins and their receptors in animal sebaceous model systems is not necessarily predictive of their role in a human sebaceous lipid regulation.

Eisinger, M., et al., in U.S. Pat. No. 7,049,331, issued May 23, 2006 disclose 1,2,4-thiadiazole derivatives useful as melanocortin receptor modulators. Eisinger, M., et al., in U.S. Pat. No. 7,319,107, issued Jan. 15, 2008 disclose thiadiazolium derivatives useful as melanocortin receptor modulators.

SUMMARY OF THE INVENTION

The present invention is directed to a method for the treatment of a disorder mediated by the melanocortin-5 receptor, preferably a dermatological disorder, comprising administering to a subject in need thereof a therapeutically effective amount of a compound of formula (I)

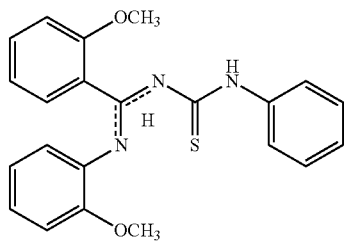

(I)

or pharmaceutically acceptable salt thereof.

The present invention is further directed to a method for the treatment of a disorder mediated by the melanocortin-5 receptor, comprising administering to a subject in need thereof a therapeutically effective amount of a compound of formula (Ia)

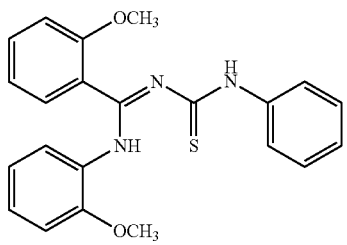

(Ia)

or pharmaceutically acceptable salt thereof, also known as 1-[(2-methoxy-phenyl)-(2-methoxy-phenylamino)-methylene]-3-phenyl-thiourea;

or its corresponding tautomeric form, a compound of formula (Ib)

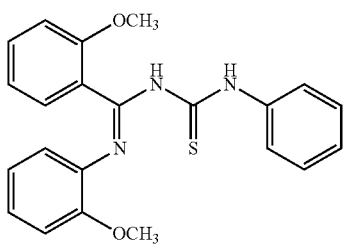

(Ib)

or a pharmaceutically acceptable salt thereof, also known as 1-[(2-methoxy-phenyl)-(2-methoxy-phenylimino)-methyl]-3-phenyl-thiourea.

The present invention is further directed to a pharmaceutical composition comprising a pharmaceutically acceptable carrier and the compound of formula (I) or pharmaceutically acceptable salt thereof. An illustration of the invention is a pharmaceutical composition made by mixing the compound of formula (I) or pharmaceutically acceptable salt thereof and a pharmaceutically acceptable carrier. Illustrating the invention is a process for making a pharmaceutical composition comprising mixing the compound of formula (I) or pharmaceutically acceptable salt thereof and a pharmaceutically acceptable carrier.

In an embodiment, the present invention is directed to a method for the treatment of a disorder mediated by the melanocortin-5 (MC5) receptor, comprising administering to a subject in need thereof, a therapeutically effective amount of any of the compounds or pharmaceutical compositions described herein. An embodiment of the present invention is the use of a compound or pharmaceutical composition as described herein for the treatment of a dermatological disorder.

An example of the invention is a method for treating a disorder selected from the group consisting of acne, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder comprising administering to a subject in need thereof a therapeutically effective amount of any of the compounds or pharmaceutical compositions described above.

Another example of the invention is the use of a compound of formula (I) or pharmaceutically acceptable salt thereof, in the preparation of a medicament for treating: (a) acne, (b) aged skin, (c) seborrheic dermatitis, (d) rosacea, (e) excessive ear wax, (f) meibomian gland disorder, (g) pseudofolliculitis, (h) yeast infections, (i) dandruff, (j) hidradenitis suppurativa, (k) ocular rosacea or (l) eccrine gland disorder, in a subject in need thereof.

DETAILED DESCRIPTION OF THE INVENTION

The present invention is directed to methods for the treatment of disorders mediated by the melanocortin-5 receptor, preferably, dermatological disorders mediated by the melanocortin-5 receptor, comprising administering to a subject in need thereof a therapeutically effective amount of a compound of formula (I) or pharmaceutically acceptable salt thereof.

The compound of formula (I) and pharmaceutically acceptable salts thereof, are useful as intermediates in the synthesis of the compound of formula (II)

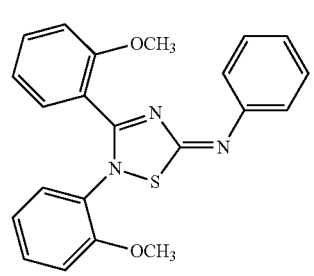

(II)

and pharmaceutically acceptable salts thereof; and in the synthesis of the compound of formula (III)

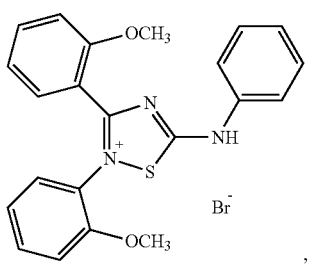

(III)

and pharmaceutically acceptable salts thereof; as disclosed in Eisinger, M., et al., U.S. Pat. No. 7,049,331, issued May 23, 2006; and Eisinger, M., et al., in U.S. Pat. No. 7,319,107, issued Jan. 15, 2008; which are hereby incorporated by reference in their entirety herein. Surprisingly, the compound of formula (I) has also been found to be a human metabolite of the compound of formula (II) and the compound of formula (III).

One skilled in the art will recognize that the compound of formula (I) may alternatively be drawn as one of two alternate tautomeric structures, more particularly, as the compound of formula (Ia)

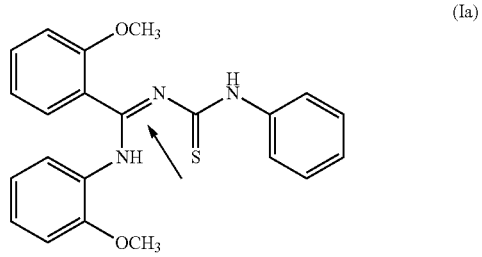 [SMILES: COc1ccccc1N/C(=N\C(=S)Nc1ccccc1)c1ccccc1OC]

(Ia)

or the compound of formula (Ib)

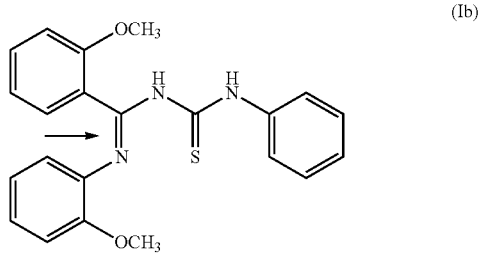 [SMILES: COc1ccccc1/N=C(/NC(=S)Nc1ccccc1)c1ccccc1OC]

(Ib)

wherein the double bond denoted by an arrow (in the structure drawn above) shifts between two positions. One skilled in the art will further recognize that it may not be possible to determine exactly in which orientation the compound of formula (I) is prepared and/or isolated, and further that the compound of formula (I) may in fact be prepared and/or isolated as a mixture of the two tautomeric structures. One skilled in the art will further recognize that tautomeric structures such as those of the compound of formula (Ia) and the compound of formula (Ib) may alternatively be designated by the use of a dashed line at both double bond positions, as is drawn for the compound of formula (I). Thus the presence of the two tautomeric structures—the compound of formula (Ia) and the compound of formula (Ib)—may be designated the single structure, a compound of formula (I)

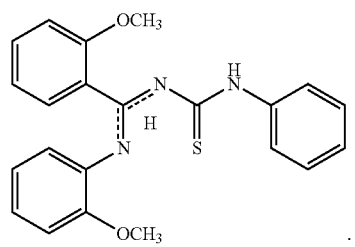

(I)

The present invention is further directed to a method of treating a disorder mediated by the melanocortin-5 receptor, preferably a disorder which is susceptible to treatment by agonism or antagonism of the melanocortin-5 receptor. More preferably, the disorder mediated by the melanocortin-5 receptor is a dermatological disorder as herein defined. More preferably still, the disorder mediated by the melanocortin-5 receptor is acne.

As used herein, unless otherwise noted, the term "dermatological disorders" include, but are not limited to, acne, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder. Preferably, the dermatological disorder is acne.

As used herein, unless otherwise noted, the term "isolated form" shall mean that the compound is present in a form which is separate from any solid mixture with another compound(s), solvent system or biological environment. In an embodiment of the present invention, the compound of formula (I) or its pharmaceutically acceptable salt is an isolated form.

As used herein, unless otherwise noted, the term "substantially pure compound" shall mean that the mole percent of impurities in the isolated compound or pharmaceutically acceptable salt thereof is less than about 5 mole percent, preferably less than about 2 mole percent, more preferably, less than about 0.5 mole percent, most preferably, less than about 0.1 mole percent. In an embodiment of the present invention, the compound of formula (I) or its pharmaceutically acceptable salt is substantially pure.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is substantially free of corresponding salt form(s).

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The present invention further comprises pharmaceutical compositions containing one or more of the compounds or pharmaceutically acceptable salts thereof as described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg or any range therein, and may be given at a dosage of from about 0.01-300 mg/kg/day, or any range therein, preferably from about 0.5-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by a melanocortin receptor, preferably the melanocortin-5 receptor, described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of disorders mediated by a melanocortin receptor, preferably the melanocortin-5 receptor, more preferably wherein a dermatological disorder mediated by the melanocortin-5 receptor, is required.

The daily dosage of the products may be varied over a wide range from 0.01 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any range therein. Preferably, the range is from about 0.5 to about 250.0 mg/kg of body weight per day, or any range therein. More preferably, the range is from about 0.5 to about 100.0 mg/kg of body weight per day, or any range therein. More preferably, the range is from about 0.5 to about 50.0 mg/kg of body weight per day, or any range therein. More preferably from about 1.0 to about 5.0 mg/kg of body weight per day, or any range therein. The compounds may be administered on a regimen of 1 to 4 times per day.

For topical administration, daily dosages may be varied over a wide range of from about 0.05% to about 10% (w/w), or any range therein. An effective amount of the drug may be supplied in a cream formulation at for example a dosage level of about 0.05% to about 10% (w/w), or any range therein; preferably about 0.1% to about 5% (w/w), or any range therein; more preferably about 0.5% to about 2.5% (w/w), or any range therein; more preferably at about 1.0% to about 2.0% (w/w), or any range therein; for example at about 1.2% (w/w). As an example, the daily dosage, assuming a total body surface of 1.62 m$^2$, may be, for example, about 1.0 to about 50 mg/m$^2$/day, or any range therein, preferably about 5.0 to about 25 mg/m$^2$/day, or any range therein, more preferably about 7.5 to about 20 mg/m$^2$/day, or any range therein. The compound further may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Preparation of the Compound of Formula (I)

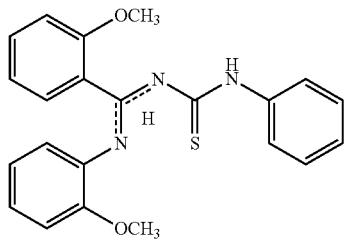

Step A:

A mixture of o-anisidine (13.5 g, 110.0 mmol) and sodium amide (50 wt. % suspension in toluene) (9.40 g, 120.0 mmol) in anhydrous toluene (200 ml) was stirred for 1 hour at room temperature. To the mixture was added 2-methoxybenzonitrile (16 ml, 131.0 mmol) and the reaction mixture was then heated under reflux for 16 hours. The reaction mixture was cooled and 1.0N HCl (150 ml) was added to quench the reaction. Activated carbon was added and the reaction mixture was filtered through a Celite pad. The pH of the mixture was adjusted to about 14 by addition of 1.0 N NaOH (200 ml). The aqueous layer was extracted with chloroform (3×150 ml). The combined organic layer was dried over anhydrous $MgSO_4$, and evaporated. The resulting solid was washed with hexane and dried over the vacuum to yield the product as a pale white solid. MS (APCl, $MH^+$) 257

Step B:

A mixture the pale white solid prepared as in STEP A above (15.5 g, 60.6 mmol) and phenylisothiocyanate (8.70 mL, 72.7 mmol) in anhydrous chloroform (30 ml) was heated at 45° C. for 16 hours. The reaction mixture was cooled and the solvent was evaporated. The resulting residue was purified by flash column chromatography with a mobile phase of 25% hexane in dichloromethane. The combined fractions were evaporated and the resulting solid was dried over vacuum to yield the title compound as a yellow solid. MS (ESI, $MH^+$) 391.50

Example 2

Preparation of the Compound of Formula (I)

The compound of formula (I) was alternatively prepared according to the process as outlined in Step A and Step B below.

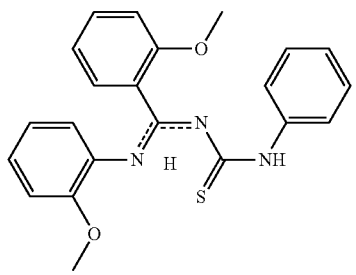

Step A:

To a 500 ml 4 neck double jacket reaction glass vessel $NaNH_2$ (41.60 g, 1.07 mol) was suspended under nitrogen in toluene (200 ml) at room temperature. The resulting mixture was cooled to 20° C. A mixture of 2-methoxy-benzonitrile (64.04 g, 0.52 mol) and o-anisidine (77.68 g, 0.58 mol) was added dropwise over 40 minutes, by syringe. During the addition the colour of the mixture became dark grey. Gas development and an increase in temperature (of about 5° C.) was observed. The resulting mixture was stirred for 4 hours at 20° C. The resulting mixture was then chilled to −6° C. To the cooled mixture was then added conc. HCl (32%, 58.76 g) diluted with water (117.52 g) dropwise over 45 minutes, by syringe. A brown precipitate was observed during the addition and the internal temperature increased to about 12° C. The precipitate was filtered off and triturated at ambient temperature with $EtOH/H_2O$ (1:1, 300 g) followed by cyclohexane (300 g) to yield a beige solid. The solid was dried at 45° C./50 mbar for 15 h.

Step B:

A 100-ml 4-neck double-jacket glass vessel was charged with N-(2-methoxyphenyl)-2-methoxybenzamidine (the beige solid prepared as in STEP A above; 12.82 g, 0.05 mol), in toluene (26.01 g). To the resulting pale beige suspension was then added phenylisothiocyanate (6.75 g, 0.05 mol) over 2 minute, while stirring to maintain the internal temperature at about 30° C. The resulting yellow mixture was stirred for 24 hours to yield the title compound in solution, as determined by HPLC analysis.

Example 3

Prophetic Example Alternative Synthesis of the Compound of Formula (I)

The compound of formula (I) may alternatively be prepared according to the process as outlined in the Scheme below.

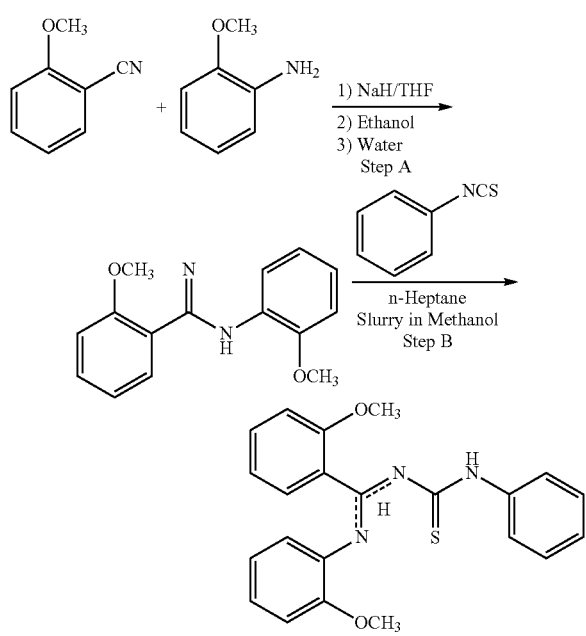

Example 4

In Vitro Assay

Measurement of Regulation of Sebaceous Lipid Synthesis

Step A: Preparation of a Feeder Layer

Semiconfluent cultures of 3T3 mouse fibroblasts (Swiss Albino mouse, ATCC CCL-92) were treated with mitomycin C (4 µg/ml) for 3 hours, trypsinized and seeded at a density of $2.5 \times 10^5/9.5 \text{ cm}^2$ tissue culture plate in Dulbeccos Minimal Essential Medium (DMEM) containing 10% Colorado Calf Serum, penicilin (100 U/ml), streptomycin (100 µg/ml), L glutamine (0.3 mg/ml), sodium pyruvate (1 mM) and nonessential amino acids (100 µM). The cells were incubated at 37° C. for 24 hours prior to their use as a feeder layer for sebocytes.

Step B: Isolation of Human Sebocytes

Human sebocytes were isolated from Dermatome shavings of postoperative pieces of human skin at 0.4-0.8 mm depths (this part of the skin was previously shown to be enriched in sebaceous glands). Shavings so obtained were treated with 1% Dispase in Iscoves medium containing 10% serum for 20 min at 37° C. The tissue was then placed in 0.3% trypsin/1% EDTA in Phosphate Buffered Saline (PBS) for 10 minutes at 37° C. Following this incubation the cells were gently scraped from the tissue in Growth medium (GM) containing DMEM/F12 media mixture (3:1), supplemented with 8% heat inactivated FBS, 2% heat inactivated human serum (HS), 1 mM sodium pyruvate, epidermal growth factor (10 ng/ml), insulin (10 µg/ml), hydrocortisone (0.4 µg/ml), L-glutamine, antibiotics, and +/−cholera toxin (1.2 nM). Cells so obtained were filtered through nylon mesh (100 µm pore size), centrifuged at 750 RPM, re-suspended in GM and counted.

Step C: Cultures of Human Sebocytes

Resultant cells from the above isolation procedure were plated on the 3T3 feeder layers at $2 \times 10^5/9.5 \text{ cm}^2$ in growth medium and maintained at 37° C. and 5% $CO_2$ for 3 days (Phase I). Following the initial growth period they were transferred to a transition medium (TM) that consisted of DMEM/F12 media supplemented with 1 mM sodium pyruvate, insulin (10 µg/ml), transferrin (6.7 ng/ml) and selenium (5.5 µg/ml) (ITS), 2% heat inactivated FBS and 2% heat inactivated human serum, L-glutamine and antibiotics, and +/−cholera toxin (1.2 nM) (Phase II). Three days later the cells were changed to differentiation medium (DM), DMEM/F12 supplemented with ITS, 3,3',5-triido-L-thyronine sodium(3 nM), 1% (v/v) trace element mix and the choice of differentiation agent, i.e. bovine pituitary extract (10 µg/ml) or cholera toxin (1.2 nM). This medium was changed every 3 days (Phase III).

Step D: testing stimulators or inhibitors of sebocyte differentiation and lipid Production Hormones, mixture of hormones (i.e. bovine pituitary extract) or compounds to be tested were added to the culture at the beginning of phase III. Two criteria were used to evaluate the effect of these materials on sebaceous cultures: 1) visual observations and 2) evaluation of sebaceous lipid accumulation and synthesis. One assay for lipid accumulation used Nile red, a fluorescent dye. This method relies on visualization of neutral lipids by Nile red and quantitation by reading of fluorescence at 535 nm excitation, 580 nm emission using a plate reader. The lipid synthesis was also evaluated by radioactive labeling using $^{14}C$ acetate and quantified by Bio Rad Phosphoimager (Molecular Imager, FX) using Quantity One 4.1 software.

Step E: Visual Observations & Nile Red Evaluation of Lipid Accumulation

Morphological evaluation of lipid accumulation was easily recognized since the cells enlarged and displayed lipid granules that in bright field light microscopy appeared as yellowish circles in the cells. Quantitation of accumulation/inhibition of neutral lipids in sebocytes was accomplished by Nile red binding assay. Briefly, following exposure of sebocytes to test compounds, the cells were allowed to interact with 1 µM Nile red in Hanks buffered saline solution containing DMSO and Pluronic F127. After 4 hours of incubation, washing and incubation overnight, the fluorescence was read at 535 excitation and 580 emission using a fluorescence plate reader. To determine whether the compounds had an inhibitory effect on cell growth, cell counts were performed.

Step F: Evaluation of Sebaceous Lipid Synthesis by Sebaceous Cells

At day 11 of the culture, sebocytes were labeled with $^{14}C$ acetate at a final concentration of 2 µCi/ml for 24 hours in serum free culture medium. The cells were than scraped from plates and frozen at −80° C. in glass vials. Lipid extraction was completed using the Bligh-Dyer method (Bligh, E. G. and Dyer, W. J., Can. *J. Biochem. Physiol.*, 1959, 37, pp 911-916) with slight modification as detailed herein. Briefly, cells were homogenized in a 2:1 chloroform-methanol mixture, in the presence of KCl. The organic phase was removed from the mixture, the separated lipids were dried under argon and spotted to high performance thin layer chromatography (HPTLC) plates. The plates were developed by three separate mobile phases. The first was hexane (to the top of the plate), followed by toluene (to the top) and finally a 70:30:1 mixture of hexane:ether:acetic acid (half way up the plate-10 cm). To quantify the amount of radioactivity in each lipid fraction, a Bio-Rad Phosphoimager (Molecular Imager FX) with Quantity One 4.1 software was used. For visualization of unlabeled lipids the plates were sprayed with 8% cupric acid and charred on a hot plate. Quantization of the results was done by Image Pro Plus 3.0 (Media Cybernetics, Silver Springs, Md.).

The compound of formula (I) was tested according to the procedure as described above, using sebaceous cells and cholera toxin as the inducer of lipid synthesis. Three representative % Inhibition results are given in Table 1 and Table 2, below.

TABLE 1

Nile Red Evaluation of Lipid Accumulation

| Concentration of Compound (I) (µM) | % Inhibition (Nile Red Fluorescence) |
|---|---|
| — | 0% |
| 0.4 | 24% |
| 0.6 | 25% |
| 0.8 | 39% |
| 1.0 | 45% |
| 1.2 | 43% |

TABLE 2

% Inhibition of Sebaceous Lipid Synthesis

| Lipid | @ 0.4 µM | @ 0.8 µM | @ 1.2 µM | @ 1.6 µM | @ 3.2 µM |
|---|---|---|---|---|---|
| | | % Inhibition Study 1 | | | |
| squalene | NT | 50% | 55% | 62% | 76% |
| cholesterol esters | NT | 30% | 35% | 45% | 60% |
| triglycerides | NT | 0% | 10% | 8% | 2% |
| | | % Inhibition Study 2 | | | |
| squalene | 64% | 88% | 92% | 94% | 96% |
| cholesterol esters | 44% | 64% | 72% | 74% | 86% |
| triglycerides | 22% | 20% | 16% | 14% | 6% |

NT = not tested

Example 5

In Vitro Assay

Melanocortin-5 (MC-5) Receptor Binding Assays

Binding to the MC-5 receptor was measured in two assays, performed by CEREP and MDS-PANLABS.
CEREP Assay:
The assay run by CEREP (Catalog Ref. #889-5h) used human recombinant CHO cells, $[^{125}I]$NDP-α-MSH as the ligand (0.05 nM concentration), NDP-α-MSH as the nonspecific (1 µM), incubating at 37° C. for 60 min and detecting binding via scintillation counting. The specific ligand binding to the receptors was defined as the difference between the total binding and the nonspecific binding determined in the presence of an excess of unlabelled ligand. The $IC_{50}$ values (the concentration causing a half-maximal inhibition of control specific binding) and Hill coefficients were determined by non-linear regression analysis of the competition curves generated with mean replicate values using Hill equation curve fitting $(Y=D+[(A-D)/(1+(C/C_{50})^{nH})]$, where Y=specific binding, D=minimum specific binding, A=maximum specific binding, C=compound concentration, $C_{50}=IC_{50}$, and nH=slope factor). This analysis was performed using software developed at CEREP (Hill software) and validated by comparison with data generated by the commercial software SigmaPlot® 4.0 for Windows® (© 1997 by SPSS Inc.). The inhibition constants $(K_i)$ were calculated using the Cheng Prusoff equation $(K_i=IC_{50}/(1+(L/K_D))$, where L=concentration of radioligand in the assay, and $K_D$=affinity of the radioligand for the receptor).

MDS-PANLABS Assay:
The assay run by MDS-PANLABS (Catalog Ref #251400) used human recombinant HEK-293 cells, $[^{125}I]$NDP-α-MSH as the ligand (0.035 nM), various concentrations of the compound of formula (I), incubating at 37° C. for 60 min, and detecting binding via scintillation counting. Specific ligand binding to the receptors was defined as the difference between the total binding and the nonspecific binding determined in the presence of an excess (3 µM) of unlabelled NDP-α-MSH. $IC_{50}$ values were determined by a non-linear, least squares regression analysis using Data Analysis Toolbox. Inhibition constants (Ki) were calculated using the equation of Cheng and Prusoff (Biochem. Pharmacol. 22:3099, 1973) using the observed $IC_{50}$ of the tested compound, the concentration of radioligand employed in the assay, and the historical values for the Kd of the ligand (obtained experimentally at MDS Pharma Services).
Results:
The compound of formula (I) was tested for binding to the MC-5 receptor in both the CEREP and MDS-PANLABS assays with results as listed in Table 3 below.

TABLE 3

MC-5 Binding

| Assay ID | $IC_{50}$ (µM) | $K_i$ (µM) |
|---|---|---|
| CEREP | 57 | 53 |
| MDS-PANLABS | 1.17 | 1.10 |
| MDS-PANLABS | 3.53 | 3.31 |
| MDS-PANLABS MEAN ± SD | 2.35 ± 1.67 | 2.20 ± 1.56 |

Example 6

Prophetic Example

Topical Formulations

A: Microemulsion
A microemulsion composition is prepared by blending the following components, with heating as need:

| | |
|---|---|
| Polysorbate 60 | 20 parts |
| (e.g Tween 60 from ICI Surfactants) | |
| Isopropyl Palmitate | 20 parts |
| Sorbitan Oleate | 13 parts |
| (e.g. Span 80 from ICI Surfactants) | |
| 2-Ethylhexanediol-1,3 | 4 parts |
| Butylated hydroxy-toluene (BHT) | 0.05 parts |
| Compound of formula (I) | 0.1 parts |

To the blended mixture is then slowly added water (42.9 parts by weight), with mixing as necessary, to yield the emulsion.
B: Hydroalcoholic Gel
As a specific embodiment of a hydroalcoholic gel composition the polypropylene glycol (10 parts by weight), butylene glycol (10 parts by weight), benzyl alcohol (2 parts by weight), ethylenediaminetetraacetic acid (EDTA) (0.05 parts by weight) and BHT (0.05 parts by weight) are mixed with water (74.85 parts by weight total). The mixture is blended until all the components are dissolved. Carbomer (e.g. Carbopol 934P from Goodrich) (3 parts by weight) is then slowly added with constant turning to yield a gel. The compound of formula (I) (0.05 parts by weight) is then dispersed into the gel with mixing. The gel pH is adjusted to about pH 3-4.

C: Anhydrous Gel

As a second specific embodiment of an anhydrous gel isopropanol (20 parts by weight) is added to butylene glycol (20 parts by weight). BHT (0.05 parts by weight) and benzyl alcohol (1.0 parts by weight) are then added to the isopropanol/butylene glycol mixture. To the resulting mixture is then added Cyclotetrasiloxane ($D_4$) and Organopolysiloxane-11 (e.g. Gransil GSM Gel from Grant Industries) (58.85 parts by weight) with continuous mixing. The compound of formula (I) (0.1 parts by weight) is micronized and dispersed into the gel with continuous mixing until uniformly distributed.

D: Cream

As yet another specific embodiment of an o/w (oil/water) cream, the following components are mixed in the amounts (parts by weight) as noted. The final mixture is adjusted to about pH 2 with hydrochloric acid.

| | |
|---|---|
| Cetearyl alcohol | 4.3 parts |
| Microcrystalline wax | 9.0 parts |
| Ceteth-20 Surfactant (e.g. Brij 58 from ICI Surfactants)) | 1.1 parts |
| Capric/Caprylic Triglycerides (e.g. Tegosoft CT from GoldSchmidt) | 3.6 parts |
| Glycine | 0.6 parts |
| Compound of formula (I) | 0.1 parts |
| BHT | 0.05 parts |
| Water | 81.25 parts |

Example 7

Prophetic Example

Oral Formulation

As a specific embodiment of an oral composition, 100 mg of the compound of formula (I) is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for the treatment of a disorder mediated by the melanocortin-5 receptor comprising administering to a subject in need thereof a therapeutically effective amount of a compound of formula (I)

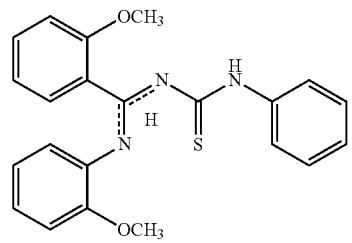

(I)

or pharmaceutically acceptable salt thereof.

2. A method as in claim 1, wherein the disorder mediated by the melanocortin-5 receptor is a dermatological disorder.

3. A method as in claim 2, wherein the dermatological disorder is selected from the group consisting of acne, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder.

4. A method as in claim 3, wherein the dermatological disorder is acne.

5. The method according to claim 1 wherein the subject is a human being.

6. The method according to claim 1 wherein the compound is

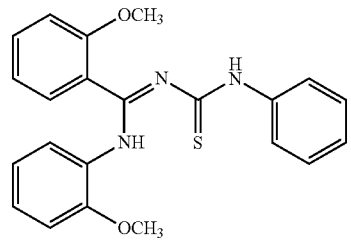 [SMILES: COc1ccccc1N/C(=N\C(=S)Nc1ccccc1)c1ccccc1OC]

or pharmaceutically acceptable salt thereof.

7. The method according to claim 1 wherein the compound is

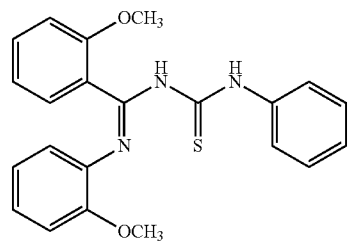 [SMILES: COc1ccccc1/N=C(/NC(=S)Nc1ccccc1)c1ccccc1OC]

or pharmaceutically acceptable salt thereof.

* * * * *